US010688278B2

(12) United States Patent
Beeckler et al.

(10) Patent No.: US 10,688,278 B2
(45) Date of Patent: Jun. 23, 2020

(54) CATHETER WITH PRESSURE MEASURING TIP (75) Inventors: Christopher Thomas Beeckler, Brea, CA (US); Assaf Govari, Haifa (IL); Yaron Ephrath, Karkur (IL)

(73) Assignee: Biosense Webster (Israel), Ltd., Yokneam (IL)

(*) Notice: Subject to any disclaimer, the term of this patent is extended or adjusted under 35 U.S.C. 154(b) by 240 days.

(21) Appl. No.: 12/627,327

(22) Filed: Nov. 30, 2009

(65) Prior Publication Data
US 2011/0130648 A1    Jun. 2, 2011

(51) Int. Cl.
*A61M 25/00* (2006.01)
*A61B 18/14* (2006.01)
*A61B 18/00* (2006.01)
*A61B 90/00* (2016.01)
*A61B 34/20* (2016.01)

(52) U.S. Cl.
CPC ..... *A61M 25/0054* (2013.01); *A61B 18/1492* (2013.01); *A61B 2018/00351* (2013.01); *A61B 2034/2051* (2016.02); *A61B 2090/064* (2016.02); *A61M 25/0069* (2013.01)

(58) Field of Classification Search
USPC ............... 600/431, 433, 424, 423, 434, 394
See application file for complete search history.

(56) References Cited

U.S. PATENT DOCUMENTS

| 3,841,150 A | 10/1974 | Pearson |
| 3,971,364 A | 7/1976 | Fletcher |
| 4,764,114 A | 8/1988 | Jeffcoat et al. |
| 4,856,993 A | 8/1989 | Maness |
| 4,930,494 A | 6/1990 | Takehana et al. |
| 5,263,493 A | 11/1993 | Avitall |
| 5,368,564 A | 11/1994 | Savage |
| 5,391,199 A | 2/1995 | Ben Haim |
| 5,462,527 A | 10/1995 | Stevens-Wright et al. |

(Continued)

FOREIGN PATENT DOCUMENTS

| DE | 19750441 | 6/1999 |
| EP | 928601 A1 | 7/1999 |

(Continued)

OTHER PUBLICATIONS

Okumura, Y. et al. A Systematic Analysis of In Vivo Contact Forces on Virtual Catheter Tip-Tissue Surface Contact During Cardiac Mapping and Intervention. J of Cardiovasc Electrophysiol, vol. 19, pp. 632-640, Jun. 2008.

(Continued)

*Primary Examiner* — Jonathan Cwern
*Assistant Examiner* — Shahdeep Mohammed
(74) *Attorney, Agent, or Firm* — Lewis Roca Rothgerber Christie LLP (57) ABSTRACT

A medical probe, consisting of a flexible insertion tube, having a distal end for insertion into a body cavity of a patient, and a distal tip, which is disposed at the distal end of the flexible insertion tube is configured to be brought into contact with tissue in the body cavity. The probe also includes a coupling member, which couples the distal tip to the distal end of the insertion tube and which consists of a tubular piece of an elastic material having a plurality of intertwined helical cuts therethrough along a portion of a length of the piece.

16 Claims, 4 Drawing Sheets

(56) References Cited

U.S. PATENT DOCUMENTS

| | | | |
|---|---|---|---|
| 5,487,757 | A | 1/1996 | Truckai et al. |
| 5,499,542 | A | 3/1996 | Morlan |
| 5,542,434 | A | 8/1996 | Imran et al. |
| 5,558,091 | A | 9/1996 | Acker et al. |
| 5,563,354 | A | 10/1996 | Kropp |
| 5,662,124 | A | 9/1997 | Wilk |
| 5,673,695 | A | 10/1997 | McGee et al. |
| 5,680,860 | A | 10/1997 | Imran |
| 5,685,878 | A | 11/1997 | Falwell et al. |
| 5,728,149 | A | 3/1998 | Laske et al. |
| 5,769,843 | A | 6/1998 | Abela |
| 5,826,576 | A | 10/1998 | West |
| 5,833,608 | A | 11/1998 | Acker |
| 5,836,894 | A | 11/1998 | Sarvazyan |
| 5,860,974 | A | 1/1999 | Abele |
| 5,861,024 | A | 1/1999 | Rashidi |
| 5,902,248 | A | 5/1999 | Millar et al. |
| 5,916,147 | A | 6/1999 | Boury |
| 5,944,022 | A | 8/1999 | Nardella |
| 5,947,320 | A * | 9/1999 | Bordner et al. ............ 220/321 |
| 5,964,757 | A | 10/1999 | Ponzi |
| 5,974,320 | A | 10/1999 | Ward et al. |
| 5,983,126 | A | 11/1999 | Wittkampf |
| 6,048,329 | A | 4/2000 | Thompson et al. |
| 6,063,022 | A | 5/2000 | Ben Haim |
| 6,123,699 | A | 9/2000 | Webster, Jr. |
| 6,171,277 | B1 | 1/2001 | Ponzi |
| 6,177,792 | B1 | 1/2001 | Govari et al. |
| 6,183,463 | B1 | 2/2001 | Webster, Jr. |
| 6,198,974 | B1 | 3/2001 | Webster, Jr. |
| 6,201,387 | B1 | 3/2001 | Govari |
| 6,203,493 | B1 | 3/2001 | Ben Haim |
| 6,216,027 | B1 | 4/2001 | Willis et al. |
| 6,226,542 | B1 | 5/2001 | Reisfeld |
| 6,239,724 | B1 | 5/2001 | Doron et al. |
| 6,241,724 | B1 | 6/2001 | Fleischman et al. |
| 6,266,551 | B1 | 7/2001 | Osadchy et al. |
| 6,272,371 | B1 | 8/2001 | Shlomo |
| 6,272,672 | B1 | 8/2001 | Conway |
| 6,301,496 | B1 | 10/2001 | Reisfeld |
| 6,332,089 | B1 | 12/2001 | Acker et al. |
| 6,334,837 | B1 | 1/2002 | Hein |
| 6,335,617 | B1 | 1/2002 | Osadchy |
| 6,351,549 | B1 | 2/2002 | Souluer |
| 6,398,738 | B1 | 6/2002 | Millar |
| 6,436,059 | B1 | 8/2002 | Zanelli |
| 6,456,864 | B1 | 9/2002 | Swanson |
| 6,484,118 | B1 | 11/2002 | Govari |
| 6,551,302 | B1 | 4/2003 | Rosinko |
| 6,569,098 | B2 | 5/2003 | Kawchuk |
| 6,574,492 | B1 | 6/2003 | Ben Haim |
| 6,584,856 | B1 | 7/2003 | Biter |
| 6,602,242 | B1 | 8/2003 | Fung et al. |
| 6,612,992 | B1 | 9/2003 | Hossack |
| 6,618,612 | B1 | 9/2003 | Acker et al. |
| 6,690,963 | B2 | 2/2004 | Ben Haim et al. |
| 6,695,808 | B2 | 2/2004 | Tom |
| 6,711,429 | B1 | 3/2004 | Gilboa et al. |
| 6,727,371 | B2 | 4/2004 | Müller et al. |
| 6,814,733 | B2 | 11/2004 | Schwartz |
| 6,835,173 | B2 | 12/2004 | Couvillon, Jr. |
| 6,892,091 | B1 | 5/2005 | Ben Haim et al. |
| 6,915,149 | B2 | 7/2005 | Ben Haim |
| 6,945,956 | B2 | 9/2005 | Waldhauser et al. |
| 6,964,205 | B2 | 11/2005 | Papakostas |
| 6,973,339 | B2 | 12/2005 | Govari |
| 6,997,924 | B2 | 2/2006 | Schwartz |
| 7,077,823 | B2 | 7/2006 | McDaniel |
| 7,156,816 | B2 | 1/2007 | Schwartz |
| 7,235,070 | B2 | 6/2007 | Vanney |
| 7,297,116 | B2 | 11/2007 | Varghese et al. |
| 7,306,593 | B2 | 12/2007 | Keidar |
| 7,306,599 | B2 | 12/2007 | Karasawa et al. |
| 7,311,704 | B2 | 12/2007 | Paul et al. |
| 7,397,364 | B2 | 7/2008 | Govari |
| 7,435,232 | B2 | 10/2008 | Liebschner |
| 7,465,288 | B2 | 12/2008 | Dudney et al. |
| 7,481,774 | B2 | 1/2009 | Brockway et al. |
| 7,536,218 | B2 | 5/2009 | Govari |
| 7,604,605 | B2 | 10/2009 | Zvuloni |
| 7,662,151 | B2 | 2/2010 | Crompton, Jr. et al. |
| 7,681,432 | B2 | 3/2010 | Hay |
| 7,686,767 | B2 * | 3/2010 | Maschke ............ 600/466 |
| 7,911,315 | B2 | 3/2011 | Bradley |
| 7,914,440 | B2 | 3/2011 | Otawara |
| 7,959,601 | B2 | 6/2011 | McDaniel et al. |
| 7,984,659 | B2 | 7/2011 | Fujimoto et al. |
| 8,043,216 | B2 | 10/2011 | Matsumura |
| 8,046,049 | B2 | 10/2011 | Govari et al. |
| 8,083,691 | B2 | 12/2011 | Goldenberg et al. |
| 8,137,275 | B2 | 3/2012 | Fan et al. |
| 8,357,152 | B2 | 1/2013 | Govari et al. |
| 8,374,819 | B2 | 2/2013 | Govari et al. |
| 8,535,308 | B2 | 9/2013 | Govari et al. |
| 8,900,229 | B2 | 12/2014 | Govari et al. |
| 8,926,528 | B2 | 1/2015 | Govari et al. |
| 9,033,916 | B2 | 5/2015 | Schultz |
| 2001/0047129 | A1 | 11/2001 | Hall |
| 2001/0047133 | A1 * | 11/2001 | Gilboa et al. ............ 600/429 |
| 2002/0002329 | A1 | 1/2002 | Avitall |
| 2002/0065455 | A1 | 5/2002 | Ben Haim et al. |
| 2002/0068931 | A1 | 5/2002 | Wong et al. |
| 2002/0068866 | A1 | 6/2002 | Zikorus et al. |
| 2002/0087089 | A1 | 7/2002 | Ben-Haim |
| 2002/0165461 | A1 | 11/2002 | Hayzelden |
| 2002/0193781 | A1 | 12/2002 | Loeb |
| 2003/0088145 | A1 * | 5/2003 | Scott ............ A61N 1/406 600/8 |
| 2003/0120150 | A1 | 6/2003 | Govari |
| 2003/0120195 | A1 | 6/2003 | Milo |
| 2003/0130615 | A1 | 7/2003 | Tom |
| 2003/0158494 | A1 | 8/2003 | Dahl |
| 2003/0187389 | A1 | 10/2003 | Morency et al. |
| 2004/0049255 | A1 | 3/2004 | Jain |
| 2004/0064024 | A1 * | 4/2004 | Sommer ............ 600/374 |
| 2004/0068178 | A1 | 4/2004 | Govari |
| 2004/0097806 | A1 | 5/2004 | Hunter et al. |
| 2004/0102769 | A1 | 5/2004 | Schwartz |
| 2004/0147920 | A1 | 7/2004 | Keidar |
| 2004/0244464 | A1 | 12/2004 | Hajdukiewicz et al. |
| 2004/0254458 | A1 | 12/2004 | Govari |
| 2005/0033135 | A1 | 2/2005 | Govari |
| 2005/0080429 | A1 | 4/2005 | Freyman |
| 2005/0096590 | A1 | 5/2005 | Gullickson et al. |
| 2005/0228274 | A1 | 10/2005 | Boese et al. |
| 2005/0277875 | A1 | 12/2005 | Selkee |
| 2006/0009690 | A1 | 1/2006 | Fuimaono |
| 2006/0009735 | A1 | 1/2006 | Viswanathan |
| 2006/0015096 | A1 | 1/2006 | Hauck |
| 2006/0064038 | A1 | 3/2006 | Omata et al. |
| 2006/0074297 | A1 | 4/2006 | Viswanathan |
| 2006/0173480 | A1 | 8/2006 | Zhang |
| 2006/0184106 | A1 | 8/2006 | McDaniel et al. |
| 2006/0200049 | A1 | 9/2006 | Leo |
| 2006/0247618 | A1 | 11/2006 | Kaplan et al. |
| 2006/0276703 | A1 | 12/2006 | Fuimaono et al. |
| 2007/0021742 | A1 | 1/2007 | Viswanathan |
| 2007/0060832 | A1 | 3/2007 | Levin |
| 2007/0060847 | A1 | 5/2007 | Paul et al. |
| 2007/0100332 | A1 | 5/2007 | Paul et al. |
| 2007/0106114 | A1 | 5/2007 | Sugimoto et al. |
| 2007/0106165 | A1 | 6/2007 | Khatib et al. |
| 2007/0142749 | A1 | 7/2007 | Larkin et al. |
| 2007/0151391 | A1 | 7/2007 | Worley et al. |
| 2007/0156114 | A1 | 7/2007 | Pappone |
| 2007/0161882 | A1 | 7/2007 | Pappone |
| 2007/0167740 | A1 | 7/2007 | Grunewald et al. |
| 2007/0167804 | A1 | 7/2007 | Park et al. |
| 2007/0167818 | A1 | 7/2007 | Osborn et al. |
| 2007/0167819 | A1 | 7/2007 | Osborn et al. |
| 2007/0179492 | A1 | 8/2007 | Pappone |
| 2007/0185397 | A1 | 8/2007 | McGee et al. |
| 2007/0191829 | A1 | 8/2007 | Wallace et al. |
| 2007/0197939 | A1 | 8/2007 | Wallace et al. |

(56) References Cited

U.S. PATENT DOCUMENTS

| | | |
|---|---|---|
| 2007/0233044 A1 | 8/2007 | Ofek et al. |
| 2007/0282211 A1 | 12/2007 | Aeby et al. |
| 2008/0009750 A1 | 1/2008 | Aeby et al. |
| 2008/0015568 A1 | 1/2008 | Paul |
| 2008/0051704 A1 | 2/2008 | Patel |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0161796 A1 | 7/2008 | Cao et al. |
| 2008/0183075 A1 | 7/2008 | Govari |
| 2008/0200843 A1 | 8/2008 | Williams et al. |
| 2008/0249467 A1 | 10/2008 | Burnett et al. |
| 2008/0249522 A1 | 10/2008 | Pappone |
| 2008/0255540 A1 | 10/2008 | Selkee |
| 2008/0269606 A1 | 10/2008 | Matsummura |
| 2008/0275428 A1* | 11/2008 | Tegg ............... A61B 5/0084 604/533 |
| 2008/0275442 A1 | 11/2008 | Paul et al. |
| 2008/0275465 A1 | 11/2008 | Paul |
| 2008/0281319 A1 | 11/2008 | Paul et al. |
| 2008/0287777 A1* | 11/2008 | Li et al. ............... 600/424 |
| 2008/0288038 A1 | 11/2008 | Paul |
| 2008/0294144 A1 | 11/2008 | Leo |
| 2008/0294158 A1* | 11/2008 | Pappone et al. ......... 606/41 |
| 2009/0010021 A1* | 1/2009 | Smith et al. ............ 362/565 |
| 2009/0093806 A1* | 4/2009 | Govari ................. A61B 5/06 606/34 |
| 2009/0138007 A1 | 5/2009 | Govari |
| 2009/0158511 A1* | 6/2009 | Maze et al. ............. 4/144.1 |
| 2009/0177111 A1 | 7/2009 | Miller et al. |
| 2009/0275966 A1* | 11/2009 | Mitusina ................. 606/171 |
| 2009/0287118 A1 | 11/2009 | Malek |
| 2009/0294361 A1* | 12/2009 | Larsen .................. 210/654 |
| 2009/0306515 A1 | 12/2009 | Matsumura |
| 2009/0306650 A1* | 12/2009 | Govari ............ A61B 18/1492 606/41 |
| 2010/0010290 A1 | 1/2010 | Stephens |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein |
| 2010/0152574 A1* | 6/2010 | Erdman et al. ............. 600/424 |
| 2010/0160770 A1 | 6/2010 | Govari et al. |
| 2010/0160778 A1 | 6/2010 | Eskandari et al. |
| 2010/0168620 A1 | 7/2010 | Klimovitch |
| 2010/0168918 A1 | 7/2010 | Zhao |
| 2010/0274239 A1 | 10/2010 | Paul et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0152880 A1 | 6/2011 | Alvarez et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 | 2/2005 |
| EP | 1586281 A1 | 10/2005 |
| EP | 1690564 | 8/2006 |
| EP | 1743575 A2 | 1/2007 |
| EP | 1897581 A2 | 3/2008 |
| EP | 2047797 | 3/2008 |
| EP | 2127604 | 6/2008 |
| EP | 2000789 A2 | 12/2008 |
| EP | 1820464 | 4/2009 |
| EP | 2047797 A2 * | 4/2009 |
| EP | 2171240 | 4/2009 |
| EP | 2338411 | 9/2009 |
| EP | 2130508 B1 | 12/2009 |
| EP | 2338412 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| JP | 8243168 A | 9/1996 |
| JP | 8266486 A | 10/1996 |
| JP | 11276592 A | 10/1999 |
| JP | 2000126301 A | 5/2000 |
| JP | 2000508224 A | 7/2000 |
| JP | 2005040215 | 2/2005 |
| JP | 2005237964 A | 9/2005 |
| JP | 2006255401 A | 9/2006 |
| JP | 2007181696 A | 7/2007 |
| JP | 2009506805 A | 2/2009 |
| JP | 2005345215 | 4/2010 |
| JP | 2006064465 | 6/2011 |
| WO | WO 1994/017856 A1 | 8/1994 |
| WO | WO95/010326 | 4/1995 |
| WO | WO 1996/005768 A | 2/1996 |
| WO | WO97/029678 | 8/1997 |
| WO | WO 1997/029709 A | 8/1997 |
| WO | WO 1997/029710 A | 8/1997 |
| WO | WO03/020139 | 9/1997 |
| WO | WO 1998/029032 A | 7/1998 |
| WO | WO06/029563 | 3/2003 |
| WO | WO06/086152 | 8/2003 |
| WO | WO06/092563 | 3/2006 |
| WO | WO 2006/043884 * | 4/2006 |
| WO | WO07/082216 | 9/2006 |
| WO | WO 2006/135483 A2 | 12/2006 |
| WO | WO 2007/015139 A2 | 2/2007 |
| WO | WO07/098494 | 3/2007 |
| WO | WO 2007/025230 A2 | 3/2007 |
| WO | WO09/147399 | 5/2007 |
| WO | WO 2007/076312 A2 | 7/2007 |
| WO | WO09/085470 | 8/2007 |
| WO | WO 2007/111182 A | 10/2007 |
| WO | WO07/050960 | 11/2007 |
| WO | WO10/000897 | 12/2007 |
| WO | WO07/067938 | 1/2008 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2010/008975 A3 | 1/2010 |
| WO | WO 2011/046874 A1 | 4/2011 |

OTHER PUBLICATIONS

European Search Report Appln No. 10 25 2020 dated Mar. 21, 2011.
European Search Report Appln No. 10 25 2020.2 dated Sep. 6, 2012.
U.S. Appl. No. 11/868,733, filed Oct. 8, 2007, US-2009-0093806-A1, U.S. Pat. No. 8,357,152.
U.S. Appl. No. 12/134,592, filed Jun. 6, 2008, US-2009-0306650-A1, U.S. Pat. No. 8,437,832.

(56) References Cited

OTHER PUBLICATIONS

U.S. Appl. No. 12/207,155, filed Sep. 9, 2008, US-2010-0063478-A1, U.S. Pat. No. 9,101,734.
U.S. Appl. No. 12/327,226, filed Dec. 3, 2008, US-2009-0138007-A1, U.S. Pat. No. 8,535,308.
U.S. Appl. No. 12/342,747, filed Dec. 23, 2008, US-2010-0160770-A1.
U.S. Appl. No. 12/646,242, filed Dec. 23, 2009, US-2011-0153253-A1, U.S. Pat. No. 8,521,462.
U.S. Appl. No. 12/646,050, filed Dec. 23, 2009, US-2011-0153252-A1, U.S. Pat. No. 8,374,819.
U.S. Appl. No. 12/647,824, filed Dec. 28, 2009, US-2011-0160556-A1, U.S. Pat. No. 8,529,476.
U.S. Appl. No. 12/692,506, filed Jan. 22, 2010, US-2011-0184406-A1, U.S. Pat. No. 8,374,670.
U.S. Appl. No. 12/797,693, filed Jun. 10, 2010, US-2011-0307207-A1, U.S. Pat. No. 8,798,952.
U.S. Appl. No. 12/827,254, filed Jun. 30, 2010, US-2012-0004576-A1, U.S. Pat. No. 8,226,580.
U.S. Appl. No. 12/857,342, filed Aug. 16, 2010, US-2012-0041295-A1, U.S. Pat. No. 8,380,276.
U.S. Appl. No. 12/899,909, filed Oct. 7, 2010, US-2012-0089358-A1, U.S. Pat. No. 8,731,859.
U.S. Appl. No. 12/938,458, filed Nov. 3, 2010, US-2012-0108988-A1, U.S. Pat. No. 8,979,772.
U.S. Appl. No. 13/075,655, filed Mar. 30, 2011, US-2012-0253167-A1, U.S. Pat. No. 8,333,103.
U.S. Appl. No. 13/152,423, filed Jun. 3, 2011, US-2012-0310116-A1, U.S. Pat. No. 8,523,787.
U.S. Appl. No. 13/181,918, filed Jul. 13, 2011, US-2013-0018306-A1.
U.S. Appl. No. 13/343,024, filed Jan. 4, 2012, US-2013-0172875-A1.
U.S. Appl. No. 13/449,194, filed Apr. 17, 2012, US-2012-0259194-A1, U.S. Pat. No. 8,359,082.
U.S. Appl. No. 13/470,871, filed May 14, 2012, US-2013-0131663-A1.
U.S. Appl. No. 13/470,842, filed May 14, 2012, US-2013-0131489-A1, U.S. Pat. No. 8,818,485.
U.S. Appl. No. 13/542,090, filed Jul. 5, 2012, US-2012-0271145-A1, U.S. Pat. No. 9,101,396.
U.S. Appl. No. 13/705,518, filed Dec. 5, 2012, US-2013-0096551-A1, U.S. Pat. No. 8,784,413.
U.S. Appl. No. 13/971,955, filed Aug. 21, 2013, US-2014-0024969-A1, U.S. Pat. No. 8,900,229.
U.S. Appl. No. 13/975,778, filed Aug. 26, 2013, US-2014-0032152-A1, U.S. Pat. No. 8,990,039.
U.S. Appl. No. 14/021,125, filed Sep. 9, 2013, US-2014-0024970-A1, U.S. Pat. No. 8,529,130.
U.S. Appl. No. 14/822,057, filed Aug. 10, 2015, US-2015-0342700-A1.
Biter, William J. et al., "Magnetic Wire Strain Sensor", 33rd International Sampe Technical Conference, Nov. 5-8, 2001, vol. 33, pp. 12-23, Seattle, WA.
Biter, William J. et al., "Magnetic Wire for Monitoring Strain in Composites", Sensors, Jun. 2001, www.sensormag.com, pp. 110-114.
Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.
Instron Marketing Brochure, "Medical Device Testing Systems", Instron 2007 http://web.archive.org/web/20080318092822/http://www.instron.com.tr/wa/library/streamfile.aspx?doc=1678&downland=true.
Instron, "Series 3300 Load Frames, Reference Manual Equipment", Instron, pp. 1-5 and 1-10, 2004.
Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).
Peirs, J. et al., "Design of an Optical Force Sensor for Force Feedback during Minimally Invasive Robotic Surgery", Eurosensors XVII, 2003, pp. 1063-1066, http://mech.kuleuven.be/micro/pub/medic/Paper_Eurosensors_2003_MIS_sensorextended.pdf.
Partial European Search Report dated Sep. 18, 2009 from related European Patent Application No. 08253265.6.
Partial European Search Report dated Dec. 7, 2009 from related European Patent Application No. 09251502.2.
European Search Report dated Mar. 8, 2010 from related European Patent Application No. 09252143.4.
Partial European Search Report dated Mar. 29, 2010 from related European Patent Application No. 09252879.3.
Partial European Search Report dated Apr. 1, 2010 from related European Patent Application No. 09252721.7.
European Search Report dated Mar. 2, 2011 from related European Patent Application No. 10175931.4.
European Search Report dated Mar. 28, 2011 from related European Patent Application No. 10252189.5.
European Search Report dated Mar. 28, 2011 from related European Patent Application No. 10252191.1.
European Search Report dated May 16, 2011 from related European Patent Application No. 10252232.3.
European Search Report dated Aug. 5, 2011 from related European Patent Application No. 11158804.2.
European Search Report dated Sep. 20, 2011 from related European Patent Application No. 11250066.5.
European Search Report dated Sep. 23, 2011 from related European Patent Application No. 11169251.3.
European Search Report dated Oct. 28, 2011 from related European Patent Application No. 11171842.5.
European Search Report dated Nov. 17, 2011 from related European Patent Application No. 11177600.1.
European Search Report dated Feb. 15, 2012 from related European Patent Application No. 11182854.7.
European Search Report dated May 2, 2012 from related European Patent Application No. 11189326.9.
European Search Report dated Jun. 4, 2012 from related European Patent Application No. 12163784.7.
European Search Report dated Jul. 20, 2012 from related European Patent Application No. 12161784.9.
European Search Report dated Nov. 20, 2012 from related European Patent Application No. 12176163.9.
European Search Report dated Feb. 11, 2013 from related European Patent Application No. 11187525.8.
European Search Report dated Apr. 9, 2013 from related European Patent Application No. 13150145.4.
English translation of JP Patent Office action dated Jun. 17, 2014, issued in corresponding JP Application No. 2010-264726, 4 pages.

* cited by examiner

FIG. 1

CATHETER WITH PRESSURE MEASURING TIP

FIELD OF THE INVENTION

The present invention relates generally to invasive medical devices, and specifically to the construction of probes for insertion into body organs.

BACKGROUND OF THE INVENTION

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue.

A number of patent publications describe catheters with integrated pressure sensors for sensing tissue contact. As one example, U.S. Patent Application Publication 2007/0100332 to Saurav et al., whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

The description above is presented as a general overview of related art in this field and should not be construed as an admission that any of the information it contains constitutes prior art against the present patent application.

SUMMARY OF THE INVENTION

In an embodiment of the present invention, a medical probe includes a flexible insertion tube, having a distal end for insertion into a body cavity of a patient, and a distal tip, which is disposed at the distal end of the insertion tube and is configured to be brought into contact with tissue in the body cavity. The probe also includes a coupling member, which couples the distal tip to the distal end of the insertion tube and which includes a tubular piece of an elastic material having a plurality of intertwined helical cuts therethrough along a portion of a length of the piece.

Typically, at least one of the helical cuts includes an enlarged termination, and the enlarged termination may include a partial ellipse.

In some embodiments the plurality of helical cuts includes n cuts, where n is an integer greater than 1, and the cuts may be configured so that the tubular piece has n-fold rotational symmetry about an axis of the piece.

In a disclosed embodiment, at least one of the helical cuts subtends an angle between 360° and 720° about an axis of the tubular piece.

In one embodiment, the coupling member is configured to bend in response to pressure exerted on the distal tip when the distal tip engages the tissue, and at least one of the helical cuts has a width chosen so as to provide a predetermined angular limit on initial bending of the coupling member.

Typically, the coupling member includes a tubular part connected by a fixed connection to the tubular piece. The tubular piece may include a stem, and the fixed connection may consist of the stem welded to the tubular part.

The tubular part and the tubular piece may be arranged so as to form a common circumference thereto, and the fixed connection may include welds on the common circumference absent regions thereon proximal to respective terminations of the helical cuts.

In another embodiment, a position sensor may be within the tubular piece. Typically, the position sensor may be configured to sense a position of the distal tip relative to the distal end of the insertion tube, the position changing in response to deformation of the coupling member. Typically, the position sensor may be configured to generate a signal in response to a magnetic field, and the signal is indicative of a position of the distal tip. The probe may include a magnetic field generator within the tubular part for generating the magnetic field.

Typically, the insertion tube, the distal tip and the coupling member are configured for insertion through a blood vessel into a heart of a patient.

There is also provided, according to an alternative embodiment of the present invention, a method for performing a medical procedure, including:

inserting into a body cavity of a patient a probe, which includes a flexible insertion tube and a distal tip, which is disposed at a distal end of the insertion tube, and a coupling member, which couples the distal tip to the distal end of the insertion tube and consists of a tubular piece of an elastic material having a plurality of intertwined helical cuts therethrough along a portion of a length of the piece, and bringing the distal tip into contact with tissue in the body cavity.

Typically, the method includes ablating the tissue with which the distal tip is in contact.

There is also provided, according to a further alternative embodiment of the present invention, a method for producing a medical probe, including:

providing a flexible insertion tube, having a distal end for insertion into a body cavity of a patient, and a distal tip, which is disposed at the distal end of the insertion tube and which is configured to be brought into contact with tissue in the body cavity; and coupling the distal tip to the distal end of the insertion tube using a coupling member, which includes a tubular piece of an elastic material having a plurality of intertwined helical cuts therethrough along a portion of a length of the piece.

The present invention will be more fully understood from the following detailed description of the embodiments thereof, taken together with the drawings in which:

DETAILED DESCRIPTION OF EMBODIMENTS

Overview

Embodiments of the present invention provide a novel design of an invasive probe, such as a catheter. The probe comprises a flexible insertion tube for insertion into a body cavity of a patient. A distal tip of the probe is coupled to the distal end of the insertion tube by a coupling member. The coupling member comprises a tubular piece of elastic material with a plurality of intertwined helices, typically a double helix, cut in a portion of the piece.

The plurality of intertwined helices permit the coupling member to bend in response to pressure exerted on the distal tip when the tip engages tissue in the body cavity. The bending is significantly greater, and is more uniform, than would be achieved by a single helix cut in the coupling member, for the same exerted pressure. The greater and more uniform bending facilitates improved measurement of the pressure causing the bending. In addition, dimensions of the helices may be chosen to significantly reduce the size of the coupling member, compared to that required by a coupling member having only one helix.

Detailed Description

Figure 1:
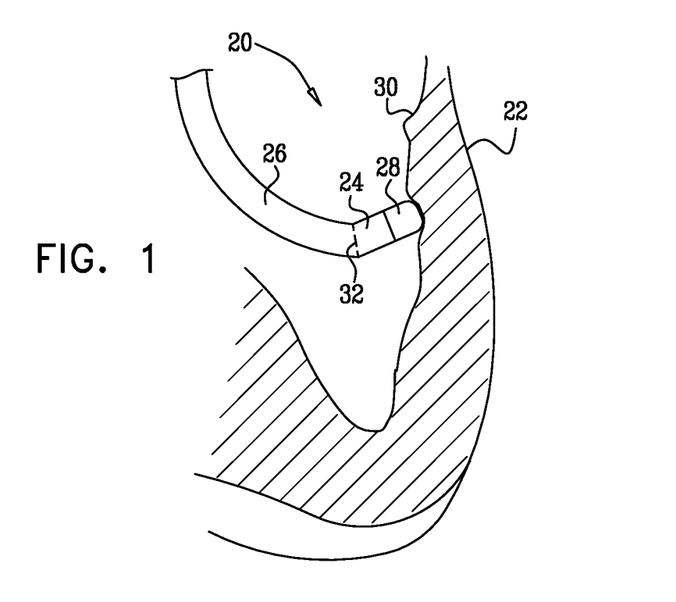
FIG. 1 is a schematic sectional view of a heart chamber with a catheter in contact with the heart wall inside the chamber, according to an embodiment of the present invention.

FIG. 1 is a schematic sectional view of a chamber of a heart 22, showing a flexible insertion tube 26 of a catheter 20 inside the heart, according to an embodiment of the present invention. The catheter is typically inserted into the heart percutaneously through a blood vessel, such as the vena cava or the aorta. An electrode 28 on a distal tip 24 of the catheter engages endocardial tissue 30. Pressure exerted by the distal tip against the endocardium deforms the endocardial tissue locally, so that electrode 28 contacts the tissue over a relatively large area. In the pictured example, the electrode engages the endocardium at an angle, rather than head-on. Distal tip 24 therefore bends at an elastic joint 32 relative to insertion tube 26 of the catheter. The bend facilitates optimal contact between the electrode and the endocardial tissue.

Because of the elastic quality of joint 32, the angle of bending of the joint is typically proportional to the pressure exerted by tissue 30 on distal tip 24 (or equivalently, the pressure exerted by the distal tip on the tissue). Measurement of the bend angle thus gives an indication of this pressure. The pressure indication may be used by the operator of catheter 20 to ensure that the distal tip is pressing against the endocardium firmly enough to give the desired therapeutic or diagnostic result, but not so hard as to cause undesired tissue damage. U.S. Patent Application 20090093806, to Govari et al., filed Oct. 8, 2007, whose disclosure is incorporated herein by reference, describes a system that uses a pressure-sensing catheter in this manner. Catheter 20 may be used in such a system.

Figure 2:
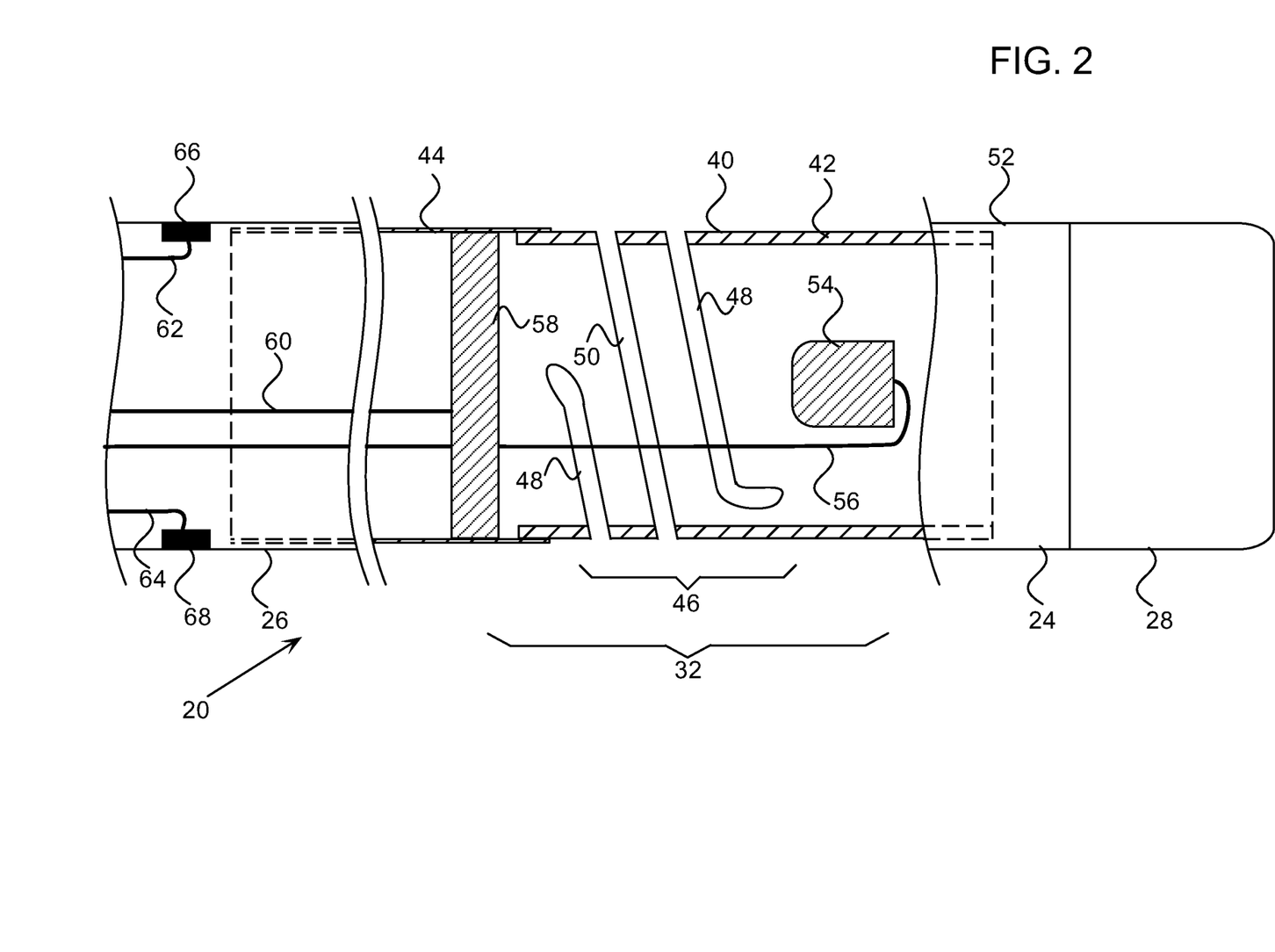
FIG. 2 is a schematic sectional view of the catheter, according to an embodiment of the present invention.

FIG. 2 is a schematic, sectional view of catheter 20, showing details of the distal end of the catheter, according to an embodiment of the present invention. A coupling member 40 forms joint 32 between distal tip 24 and the distal end of insertion tube 26. By way of example, coupling member 40 is assumed to be formed in two parts, a first part 42 and a second part 44, the two parts being fixedly joined together. The two parts of coupling member 40 are generally tubular, and are joined so that the coupling member also has a tubular form. Although there is no necessity that coupling member 40 be formed of two parts, the two part implementation simplifies assembly of a magnetic field generator and magnetic position sensor into the member, as is described in more detail below. The two part implementation is typically also facilitated by incorporating an attaching stem into one of the parts, as is also described in more detail below.

Coupling member 40 has a plurality 46 of intertwined helices cut along a portion of the length of first part 42 of the member. Plurality 46 may comprise any integral number of single helices greater than one, such as, but not limited to two, three or four helices. For simplicity, unless otherwise stated, in the following description the plurality is assumed to comprise two intertwined single cut helices, a first cut helix 48 and a second cut helix 50, and is also referred to herein as a double helix. Those having ordinary skill in the art will be able to adapt the description without undue experimentation, to encompass a plurality of intertwined helices where the plurality is more than two single helices.

Coupling member 40 (along with the distal end of catheter 20 generally) is typically covered by a flexible plastic sheath 52. When catheter 20 is used, for example, in ablating endocardial tissue by delivering RF (radio-frequency) electrical energy through electrode 28, considerable heat is generated in the area of distal tip 24. For this reason, it is desirable that sheath 52 comprises a heat-resistant plastic material, such as polyurethane, whose shape and elasticity are not substantially affected by exposure to the heat.

Catheter 20 comprises a position sensor 54 within a distal portion of first part 42. The distal portion of the first part is located within distal tip 24. The position sensor is connected via a conductor 56 to a processing unit (not shown) at the proximal end of insertion tube 26. Conductor 56 may typically comprise a twisted-pair cable. Position sensor 54 is configured to sense the position of the distal tip relative to the distal end of insertion tube 26. As explained above, the position changes in response to deformation of the coupling member, and the processing unit may thus use the position reading in order to give an indication of the pressure exerted on and by the distal tip.

For intracardiac operation, insertion tube 26 and distal tip 24 should generally have a very small outer diameter, typically of the order of 2-3 mm. Therefore, all of the internal components of catheter 20, such as conductor 56, are also made as small and thin as possible and are arranged so as to, as much as possible, avoid damage due to small mechanical strains.

Position sensor 54 may comprise one or more coils, which are configured to generate signals in response to a magnetic field. These signals are indicative of the position and orientation of distal tip 24. The magnetic field may be produced by a miniature magnetic field generator 58 located within second part 44 of the coupling member. Generator 58 is typically activated by the proximal end processing unit, via a conductor 60. Thus, when coupling member 40 bends, the signals generated by the position sensor change and can be analyzed by the processing unit to determine the pressure on the distal tip. Additional magnetic fields may be generated by field generators (not shown) in fixed locations external to the patient's body. These fields cause position sensor 54 to generate additional signals that are indicative of the position and orientation of distal tip 24 in the fixed frame of reference of the external field generators. These aspects of the operation of position sensor 54 are described in detail in the above-mentioned U.S. patent application Ser. No. 11/868,733. They are outside the scope of the present invention.

Catheter 20 typically comprises a pair of pull-wires 62, 64 for use by an operator in steering the catheter. The pull-wires pass through insertion tube 26 and are anchored at respective anchor points 66, 68 in the distal end of the insertion tube, typically on opposite sides of the tube. The operator tightens the pull-wires (typically by turning a knob—not shown—at the proximal end of the catheter) in order to bend the distal end of the catheter either "up," or "down." (The references to "up" and "down" are purely with respect to FIG. 2, and are not to be construed as limiting the motion of the catheter in any particular direction.) When the operator releases the pull-wires, the catheter straightens due to the resilience of the insertion tube.

Figure 3:
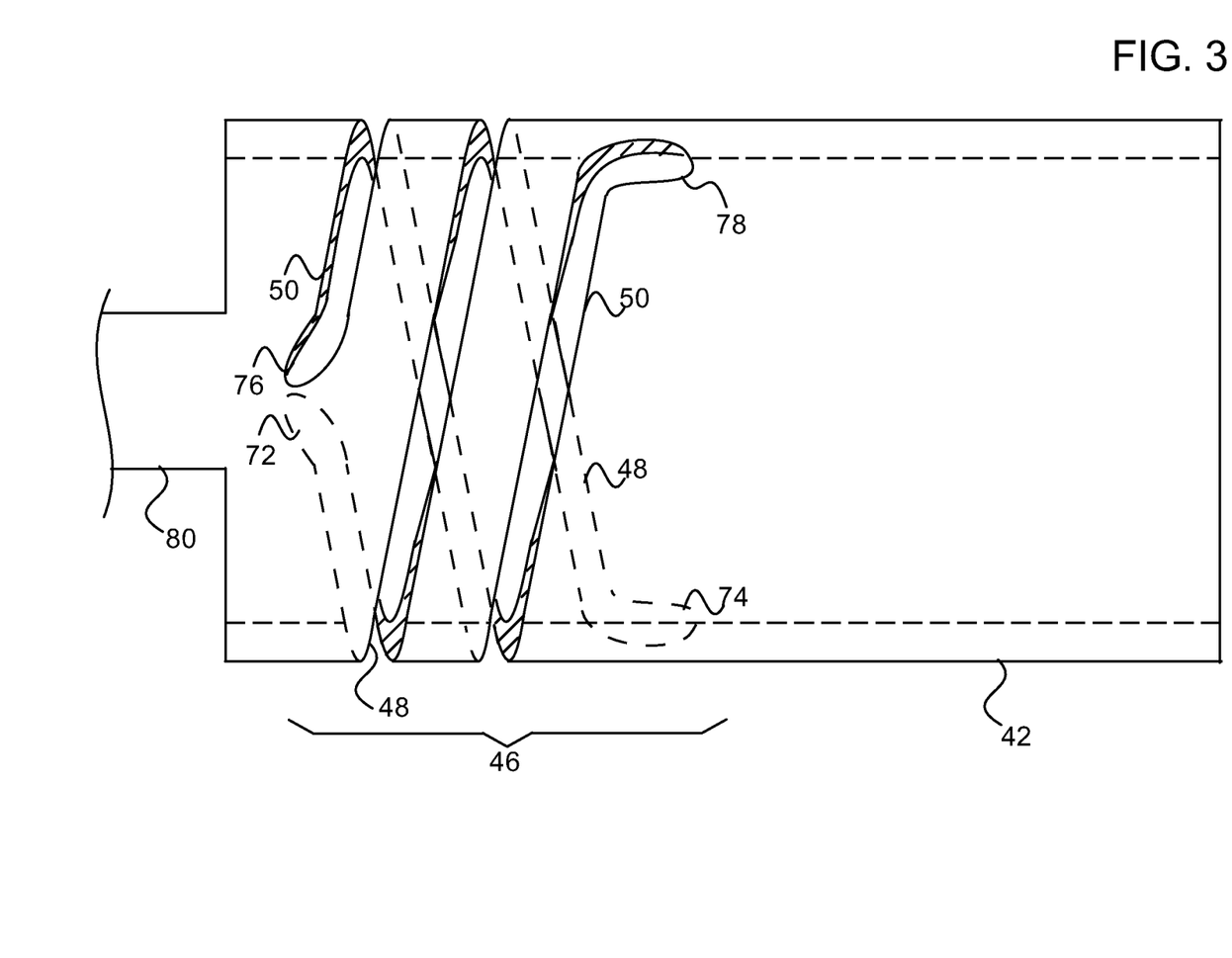
FIG. 3 is a schematic side view of a portion of a coupling member, according to an embodiment of the present invention.
Figure 4A:
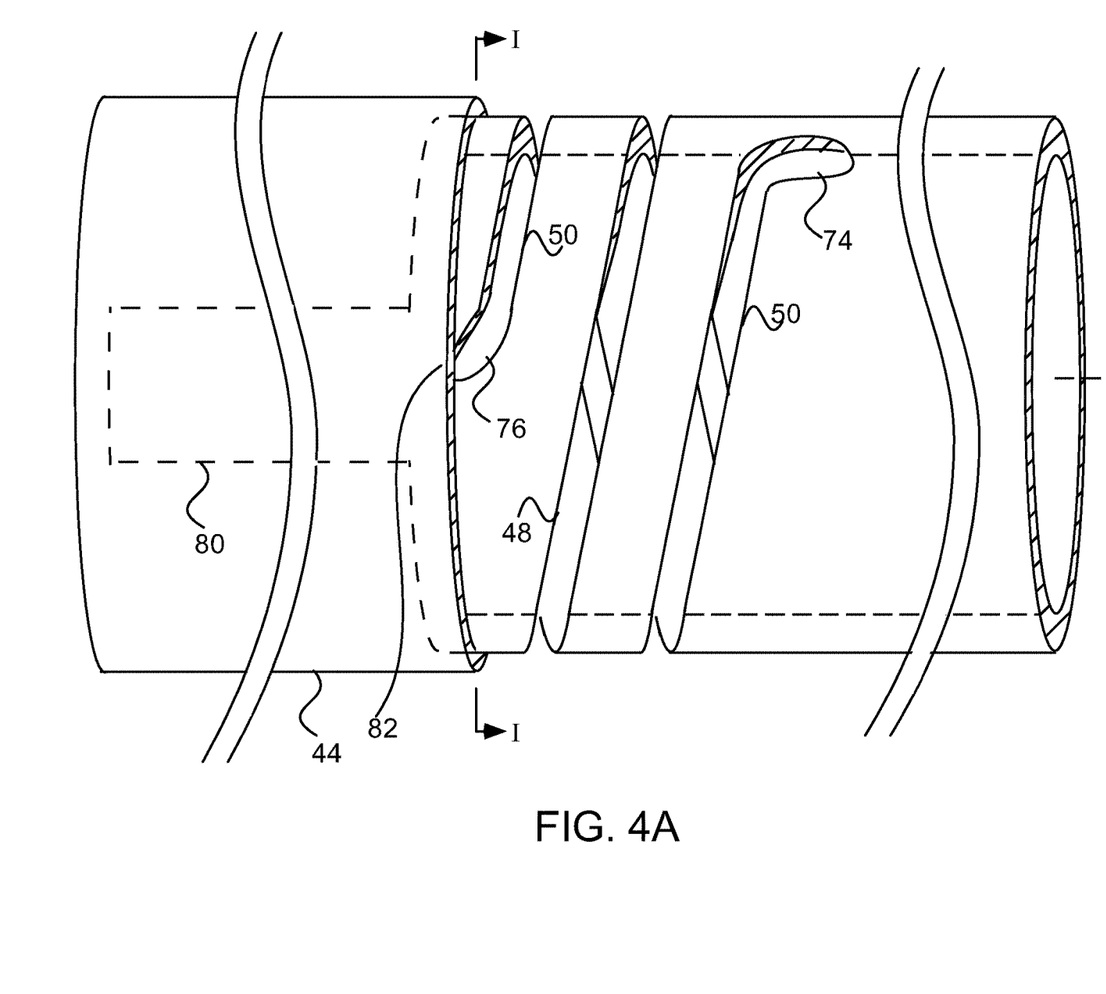
FIG. 4A is a schematic perspective view of the coupling member, according to an embodiment of the present invention.
Figure 4B:
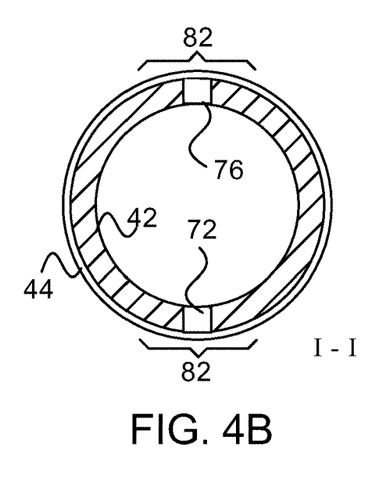
FIG. 4B is a schematic section of the coupling member, according to an embodiment of the present invention.

FIG. 3 is a schematic side view of first part 42 of coupling member 40, according to an embodiment of the present invention. FIG. 4A is a schematic perspective view of the two parts joined to form the coupling member, and FIG. 4B is a schematic section of the coupling member, according to embodiments of the present invention.

Both parts of coupling member 40 comprise generally tubular pieces of an elastic material, typically a metal material. The elastic material is typically the same for both parts, for example, a superelastic alloy such as nickel titanium (NITINOL alloy). For intracardiac applications, the overall length of member 40 may be approximately 8.5 mm, with an outer diameter of approximately 2.0 mm. Second part 44 is in the form of a cylinder having a length of approximately 5.2 mm and a wall thickness of approximately 0.08 mm. First part 42 has a wall thickness of approximately 0.27 mm. Alternatively, in other applications, the parts of coupling member 40 and its overall dimensions may be larger or smaller.

As shown in FIG. 3 and as stated above, first part of coupling member 40 has two intertwined single helices cut into the part, first helix 48 and second helix 50. The two helices may be cut by laser machining of the first part. For the dimensions given above, each helix is typically opened by the laser to a width of about 0.1 mm. While the widths of each helical cut are typically the same, there is no requirement that this is the case, and some embodiments may have the helical cuts of different widths. Furthermore, in some embodiments the width of one or both of the cuts may be varied along the cut, typically to add strength to member 40.

To give an appropriate balance between flexibility and stiffness for intracardiac applications, each helix typically subtends an angle between approximately 360° and approximately 720° about a central axis 70 (FIG. 4A) of member 40. For the intracardiac applications described above, and as illustrated in FIG. 3, each helix subtends about 450°, so that each helix has an angular extent of approximately 1.25 turns. The inventors have found that approximately 1.25 turns give a good balance between conflicting requirements of member 40, such as ensuring its radial symmetry with respect to deflection, and that the member is sufficiently strong. Alternatively, larger or smaller angular extents may be used for each helix, and the angular extents may not be equal, depending on application requirements.

The terminations of each helix of part 42 may be enlarged for the purposes of strain relief so that the part does not break during use. The enlargement is typically in the form of a partial ellipse. Thus, helix 48 terminates in a first partial ellipse 72 and a second partial ellipse 74, and helix 50 terminates in a first partial ellipse 76 and a second partial ellipse 78. In some embodiments the enlargements may be implemented as portions of circles having a diameter greater than the width of the helix. The enlargements may be oriented in relation to their respective helices so as to minimize the length of part 42, and so that, consequently, the distance between position sensor 54 and generator 58 may be minimized.

The helices of plurality 46 have rotational symmetry about axis 70, according to the number of helices in the plurality. Thus, the double helix described herein has 2-fold rotational symmetry. In general, if plurality 46 comprises n helices, where n is a positive integer, the helices are configured to have n-fold rotational symmetry about axis 70.

The configuration of the multiple helices of plurality 46 may be compared to the configuration of threads of a multiply-threaded screw, also termed a multiple-start screw. (In the same way, a single helix may be compared to the thread of a single-threaded, or single-start, screw.) Using this comparison, for the embodiment exemplified above (wherein the overall length of member 40 is approximately 8.5 mm), plurality 46 corresponds to a doubly-threaded screw having a pitch of approximately 0.5 mm, and a lead that is double this value, i.e., approximately 1.0 mm.

First part 42 typically comprises a generally rectangular stem 80, to be used in attaching part 42 to second part 44. The stem may be formed by cutting material from the tube used to produce part 42, so that the stem has the same wall thickness as the wall thickness of the remainder of part 42.

As illustrated in FIG. 4A, member 40 is formed by sliding first part 42 into second part 44, so that stem 80 is enclosed by part 44, and so that partial ellipses 72 and 76 approximately contact the edge of part 44. Once positioned as shown to have a common circumference, the two parts are then fixedly connected together, typically by keyhole welding the edges of stem 80 to the inner surface of part 44. In addition, for extra rigidity, and as shown in FIG. 4B, the two parts are also welded together where the edge of part 44 contacts part 42, i.e., around the common circumference. The circumferential welding is partial, so that regions 82, encompassing the helical cut terminations comprising partial ellipses 76 and 72, are not welded. The partial welding distributes the stresses between the two parts of the coupling member more symmetrically than that of a single helix, as well as reducing the stress at any one location by virtue of the two parts.

The plurality of helical cuts in coupling member 40 cause the member to behave as a spring, allowing the member to bend. By having more than one helical cut, the bending is more uniform than the bending (for the same range of external forces) as that of a tube with a single helical cut and the same number of turns as the plurality of cuts. The plurality of helical cuts also provide greater side stiffness compared to a tube with a single helical cut. The bending extends up to an angle, for example, 30°, at which the sides of the helical cuts on the inside of the bend come into contact. At this point, the locations in contact essentially become "inactivated," although the locations not in contact remain available for bending. The width of the helical cuts may thus be chosen to provide a desired, predetermined, angular limit on the initial bending of the coupling member, which is useful in preventing damage to components of catheter 20 that may be caused by excessive bending.

Furthermore, having a plurality of helical cuts eliminates the single point of failure that occurs with a single helical cut coupling member. Plurality 46 of helical cuts requires a corresponding plurality of failures for first part 42 of coupling member 40 to break.

Although the operation and construction of catheter are described above in the context of catheter-based intracardiac procedures, the principles of the present invention may similarly be applied in other therapeutic and diagnostic applications that use invasive probes, both in the heart and in other organs of the body. Furthermore, the principles of the implementation of catheter 20 and coupling member 40 may also be applied to enhance flexibility in catheter designs of other types, such as lasso and "Pentarray" type catheters. In a helical lasso catheter, for example, resilient elements like coupling member 40 may be incorporated into the helical lasso in order to enhance the ease of use and accuracy of alignment of the lasso in the desired position within the heart.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A medical probe, comprising:
   a flexible insertion tube, having a distal end for insertion into a body cavity of a patient;
   a distal tip having an electrode fixedly mounted thereon, which is disposed at the distal end of the flexible insertion tube and is configured to be brought into contact with tissue in the body cavity;
   a flexible coupling member separate from the electrode, which fixedly couples the distal tip to the distal end of the flexible insertion tube, the flexible coupling member having a two-piece construction, comprising a flexible tubular piece and a separate tubular part, the flexible tubular piece including an elastic member having a plurality of intertwined, single helices formed by a plurality of multiple start, longitudinally adjacent helical cuts therethrough along a portion of a length of the flexible tubular piece, wherein the intertwined, single helices subtend an angle between 360 degrees and 720 degrees about a central axis of the flexible tubular piece, the separate tubular part is configured to fit over at least a portion of the flexible tubular piece and to be fixedly connected to the flexible tubular piece and to the distal end of the flexible insertion tube, the separate tubular part and the flexible tubular piece having a common outer circumference;
   a magnetic field generator within the tubular part configured to generate a magnetic field; and
   a position sensor within the tubular piece, the position sensor configured to sense a position of the distal tip relative to the distal end of the insertion tube, the position changing in response to deformation of the coupling member and wherein the position sensor is configured to generate a signal in response to the magnetic field, wherein the signal is indicative of the relative position of the distal tip to the distal end.

2. The probe according to claim 1, wherein the plurality of intertwined helical cuts comprises n cuts, where n is an integer greater than 1, and wherein the cuts are configured so that the tubular piece has n-fold rotational symmetry about an axis of the flexible tubular piece.

3. The probe according to claim 1, wherein at least one of the helical cuts subtends an angle of 450° about the central axis of the flexible tubular piece.

4. The probe according to claim 1, wherein the flexible coupling member is configured to bend in response to pressure exerted on the distal tip when the distal tip engages the tissue, and wherein at least one of the helical cuts has a width chosen so as to provide a predetermined angular limit on initial bending of the flexible coupling member.

5. The probe according to claim 1, wherein the flexible tubular piece comprises a stem, wherein the stem has the same wall thickness as the flexible tubular piece and wherein the fixed connection comprises one or more welds between the stem and the separate tubular part.

6. The probe according to claim 1, wherein the flexible insertion tube, the distal tip and the flexible coupling member are configured for insertion through a blood vessel into a heart of the patient.

7. The probe according to claim 1, wherein at least one of the helical cuts comprises an enlarged termination.

8. The probe according to claim 7, wherein the enlarged termination comprises a partial ellipse.

9. A method for performing a medical procedure, comprising:
   inserting into a body cavity of a patient a probe, the probe comprising:
     a flexible insertion tube and a distal tip having an electrode fixedly mounted thereon, which distal tip is disposed at a distal end of the flexible insertion tube, and a flexible coupling member separate from the electrode, which fixedly couples the distal tip to the distal end of the flexible insertion tube, the flexible coupling member having a two-piece construction, comprising a flexible tubular piece and a separate tubular part, the flexible tubular piece including an elastic member having a plurality of intertwined, single helices formed by a plurality of multiple start, longitudinally adjacent helical cuts therethrough along a portion of a length of the flexible tubular piece, wherein the intertwined, single helices subtend an angle between 360 degrees and 720 degrees about a central axis of the flexible tubular piece, and the separate tubular part is configured to fit over at least a portion of the flexible tubular piece and to be fixedly connected to the flexible tubular piece and to the distal end of the flexible insertion tube, the separate tubular part and the flexible tubular piece having a common outer circumference,
     a magnetic field generator within the tubular part for generating a magnetic field, and
     a position sensor within the tubular piece, the position sensor configured to sense a position of the distal tip relative to the distal end of the insertion tube, the position changing in response to deformation of the coupling member and wherein the position sensor is configured to generate a signal in response to the magnetic field, wherein the signal is indicative of a position of the distal tip;
   bringing the distal tip into contact with tissue in the body cavity; and
   determining pressure exerted on and by the distal tip using the signal.

10. The method according to claim 9, wherein the inserting the probe comprises passing the probe through a blood vessel into a heart of the patient.

11. The method according to claim 9, further comprising ablating the tissue with which the distal tip is in contact.

12. The method according to claim 9, wherein the plurality of helical cuts comprises n cuts, where n is an integer greater than 1, and the n cuts are configured so that the flexible tubular piece has n-fold rotational symmetry about the central axis of the flexible tubular piece.

13. The method according to claim 9, wherein at least one of the helical cuts subtends an angle of 450° about the central axis of the flexible tubular piece.

14. The method according to claim 9, further comprising configuring the flexible coupling member to bend in response to pressure exerted on the distal tip when the distal tip engages the tissue, and configuring at least one of the helical cuts to have a width chosen so as to provide a predetermined angular limit on initial bending of the flexible coupling member.

15. The method according to claim 9, wherein at least one of the helical cuts comprises an enlarged termination.

16. The method according to claim 15, wherein the enlarged termination comprises a partial ellipse.

\* \* \* \* \*